United States Patent [19]

Gatten et al.

[11] Patent Number: 4,583,240
[45] Date of Patent: Apr. 15, 1986

[54] DATA ACQUISITION CIRCUITRY FOR USE IN COMPUTERIZED TOMOGRAPHY SYSTEM

[75] Inventors: Ronald A. Gatten, Placerville; Peter I. Granchukoff, Alhambra, both of Calif.

[73] Assignee: General Electric Company, Rancho Cordova, Calif.

[21] Appl. No.: 523,508

[22] Filed: Aug. 15, 1983

[51] Int. Cl.$^4$ .......................... A61B 6/00; H01J 40/14
[52] U.S. Cl. .......................................... 378/19; 378/98
[58] Field of Search .................... 378/19, 98; 250/378, 250/388, 207

[56] References Cited

U.S. PATENT DOCUMENTS

| | | | |
|---|---|---|---|
| 4,134,018 | 1/1979 | Weinkauf et al. | 378/19 |
| 4,334,154 | 6/1982 | Sandland | 378/19 |
| 4,484,340 | 11/1984 | Yamaguchi et al. | 378/19 |

Primary Examiner—Alfred E. Smith
Assistant Examiner—T. N. Grigsby
Attorney, Agent, or Firm—Flehr, Hohbach, Test, Albritton & Herbert

[57] ABSTRACT

A digital acquisition system for use in a computerized radiation tomography system employs track and hold means associated with each channel of the radiation detector in the tomography system. Each channel of the radiation detector is connected to a voltage follower transistor and resistor. A signal from the voltage follower transistor and resistor is applied through a Butterworth filter and amplifier to a transconductance amplifier which provides a signal for application to a charge storage capacitor. The capacitor is connected to the detector channel except during each limited period of time when the charge is held for measurement and conversion to a digital form. The data acquisition system has fewer components, and the simplicity of the circuitry increases the circuit reliability.

6 Claims, 2 Drawing Figures

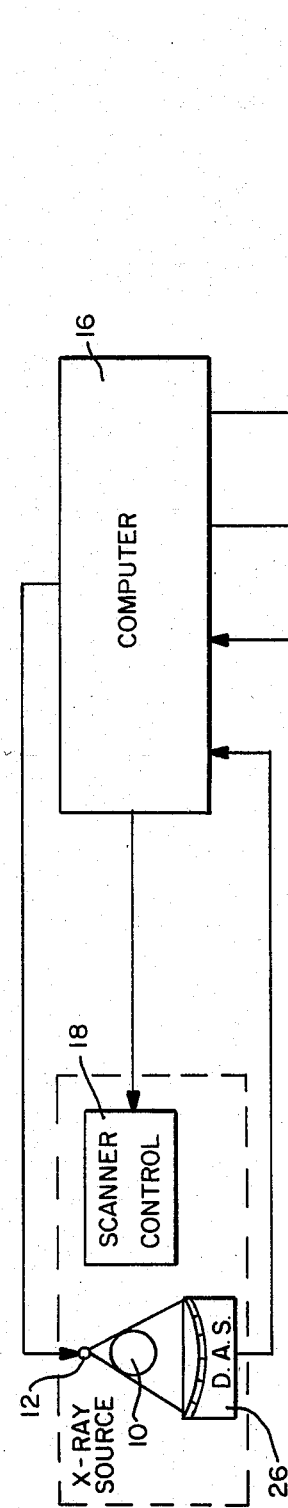
FIG.—1
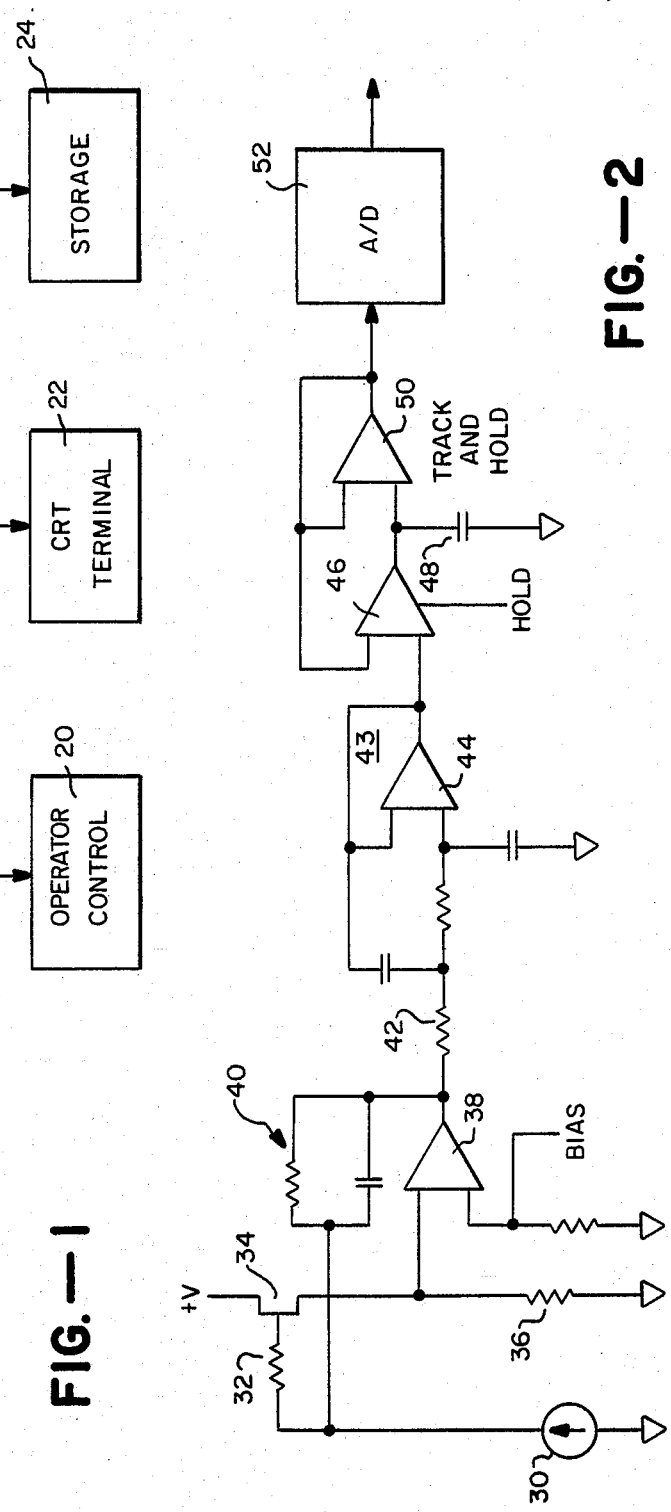
FIG.—2

DATA ACQUISITION CIRCUITRY FOR USE IN COMPUTERIZED TOMOGRAPHY SYSTEM

This invention relates generally to tomography systems, and more particularly the invention relates to data acquisition circuitry for use in a tomography system and the like.

Computerized tomography X-ray systems are used to obtain cross-sectional images of a body by obtaining a plurality of measurements of X-rays transmitted through the body at different angles relative to the body and then reconstructing the X-ray measurements to form the cross sectional image. See for example, Boyd and Goitein U. S. Pat. No. 4,075,492 for "Fan Beam X- or γ-ray 3-D Tomography".

A critical element in such a system is the data acquisition circuitry which receives an analog signal generated by an X-ray detector and provides a digital signal which is transmitted to the system computer. The conventional detector is a gas filled chamber having a plurality of voltage biased electrodes between which currents will flow in response to interaction of radiation and the gas. See for example, Boyd U.S. Pat. No. 4,075,491 for "Position Sensitive X-ray or q-ray Detector and 3-D Tomography Using Same". Heretofore, high speed sample and hold circuits have been used with multiplexer means to sample the currents generated in each channel of the detector and generate signals representative thereof. In sampling each channel a capacitor is momentarily connected thereto by multiplexer means and the resulting electrical charge on the capacitor is then converted to a digital signal by conventional analog to digital conversion means. However, the switching of the capacitor between channels introduces noise in the output signals. Further, sufficient time must be provided after connecting a capacitor to a detector channel to allow for charging of the capacitor.

An object of the present invention is improved data acquisition circuitry.

Another object of the invention is the reduction of noise in tomography data.

A feature of the invention is the use of a track and hold circuit with each detector channel to reduce noise and improve accuracy of data converted from analog to digital form.

Another feature of the invention is the use of a voltage follower transistor means connected directly with each channel of the detector.

The invention and objects and features thereof will be more readily apparent from the following detailed description and appended claims when taken with the drawing, in which:

FIG. 1 is a functional block diagram of a tomography system.

FIG. 2 is a schematic representation of data acquisition circuitry useful in the tomography system of FIG. 1 in accordance with the invention.

Referring now to the drawing, FIG. 1 is a functional block diagram of an X-ray tomography system. A body 10 to be examined is placed on a table between an X-ray source 12 and a multichannel x-ray detector 14. The X-ray scanner and table are controlled by a system computer 16 through scanner and table control circuitry 18. The computer 16 is interconnected with an operator control console 20, and electrical signals generated by the scanner are reconstructed by the computer 16 for viewing on a CRT terminal 22. Data from the scanner and computer is typically stored in archival storage means 24.

The channels of detector 14 are connected through a data acquisition system 26 to the computer 16. The data acquisition system interfaces with each channel of the detector and converts the electrical signals generated by the interaction of radiation and the confined gas of the detector into a digital signal which can be received and operated on by the computer 16. Typically, each channel of the detector has been connected through a high impedance differential transistor pair which provide a differential voltage gain to the current generated in each detector channel. The differential transistor pair also introduces some tracking voltage drift and voltage offset in the amplified output voltage.

As above described, high speed sample and hold circuits have heretofore been used with multiplexer means to sample the currents generated in each channel of the detector and generate signals representative thereof. In sampling each channel a capacitor is momentarily connected thereto and the resulting electrical charge on a capacitor is then converted to a digital signal by conventional analog to digital conversion means. However, the switching of the capacitor introduces noise in the output signals. Further, switching and charging time for the capacitor is a limiting factor.

FIG. 2 is a schematic representation of data acquisition circuitry in accordance with one embodiment of the present invention. In this embodiment the current source 30 representative of each channel of the radiation detector is connected through resistive means 32 to the gate of a field effect transistor 34. The source of transistor 34 is connected through resistor 36 to circuit ground with the source also connected to a terminal of differential amplifier 38. The other input to amplifier 38 is connected to suitable voltage bias means which provide a null offset voltage for the amplifier 38. The output of amplifier 38 is connected through a resistive-capacitive feedback 40 to the resistor 32, and the output of amplifier 38 is connected through resistive means 42 and 43 to one input of differential amplifier 44. Amplifier 44 has capacitive feedback and cooperatively functions with amplifier 38 as a three pole Butterworth filter to further minimize noise. The output of amplifier 44 is connected to one input of a transconductance switch amplifier 46 whose conductance is controlled by a HOLD signal. The output of amplifier 46 is connected to a track and hold capacitor 48 and to one input of buffer amplifier 50. The output of amplifier 50, representing the charge stored on capacitor 48 is then applied to analog to digital conversion circuitry 52 for application to the system computer.

By employing a single transistor as a voltage follower at the input of the circuitry the input is protected from possible high voltage breakdown of the detector. Importantly, the track and hold capacitor 48 is always connected to a channel of the detector, except during the sampling thereof by buffer amplifier 50, thus all data on every channel can be simultaneously latched. The simplicity of the circuit lends to its reliability.

Using a current drive to charge the storage capacitor gives improved stability and faster slewing than a voltage source such as an operational amplifier. Additionally, the transconductance amplifier 46 can be "turned off", that is, the output can be switched to a high impedance state. The output buffer 50, which is a high impedance operational amplifier, follows the voltage level of the capacitor 48 during a tracking mode and, while in the hold mold, gives a constant voltage established by the voltage stored in the capacitor during turn-off of amplifier 46. During the turn off transition the output of the buffer amplifier 50 is constantly supplying the transconductance amplifier 46 with a feedback signal such that even during this transition the tracking continues. Advantageously, this minimizes erroneous signals which are a chronic problem with sample and hold circuits.

In one embodiment the field effect transistor 34 was a 2N4117JFET, input amplifier 38 was a CA3140, transconductance amplifier 46 was a CA3080, and amplifiers 44 and 50 were CA3240. Tracking capacitor 48 was a 0.01 microfarad polyester film capacitor.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. A data acquisition circuit for use with a radiation detector and the like comprising voltage follower transistor means, amplification and filter means connected with said voltage follower transistor means, transconductance amplifier means connected to receive a signal from said amplification and filter means, charge storage means connected to receive a signal from said transconductance amplifier means, and analog to digital conversion means connected to receive charge on said charge storage means.

2. The data acquisition circuit as defined by claim 1 wherein said voltage follower transistor means includes a field effect transistor and a serially connected resistor, said amplification and filter means being connected to a common terminal of said field effect transistor and said serially connected resistor.

3. For use in measuring signals in a multichannel radiation detector and the like, a plurality of sample and hold means with each sample and hold means connected with a channel of said multiple channel radiation detector, each sample and hold means including transconductance amplifier means for receiving a signal and charge storage means connected to receive an output signal from said transconductance amplifier means.

4. The plurality of sample and hold means as defined by claim 3 wherein each sample and hold means further includes a voltage follower transistor means connected with said channel, and amplification and filter means interconnecting said voltage follower transistor means with said transconductance amplifier means.

5. The plurality of sample hold means as defined by claim 4 wherein said voltage follower transistor means includes a field effect transistor and a serially connected resistor, said amplification and filter means being connected to a common terminal of said field effect transistor and said serially connected resistor.

6. The plurality of sample and hold means as defined by claim 5 wherein said amplification and filter means includes a Butterworth filter.

* * * * *